United States Patent
Simms, Jr.

(10) Patent No.: US 8,046,060 B2
(45) Date of Patent: Oct. 25, 2011

(54) DIFFERENTIATING ARRHYTHMIC EVENTS HAVING DIFFERENT ORIGINS

(75) Inventor: Howard D. Simms, Jr., Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1379 days.

(21) Appl. No.: 11/273,079

(22) Filed: Nov. 14, 2005

(65) Prior Publication Data

US 2007/0112276 A1    May 17, 2007

(51) Int. Cl.
*A61B 5/044* (2006.01)
(52) U.S. Cl. ........................... 600/515; 600/518
(58) Field of Classification Search ............ 600/515, 600/518
See application file for complete search history.

(56) References Cited

U.S. PATENT DOCUMENTS

| | | |
|---|---|---|
| 4,006,737 A | 2/1977 | Cherry |
| 4,090,505 A | 5/1978 | Mortara |
| 4,166,470 A | 9/1979 | Neumann |
| 4,172,459 A | 10/1979 | Hepp |
| 4,187,854 A | 2/1980 | Hepp et al. |
| 4,197,850 A | 4/1980 | Schulman et al. |
| 4,223,678 A | 9/1980 | Langer et al. |
| 4,232,679 A | 11/1980 | Schulman |
| 4,236,524 A | 12/1980 | Powell et al. |
| 4,316,249 A | 2/1982 | Gallant et al. |
| 4,336,810 A | 6/1982 | Anderson et al. |
| 4,407,288 A | 10/1983 | Langer et al. |
| 4,509,530 A | 4/1985 | Curtis et al. |
| 4,527,567 A | 7/1985 | Fischler et al. |
| 4,529,401 A | 7/1985 | Leslie et al. |
| 4,531,527 A | 7/1985 | Reinhold, Jr. et al. |
| 4,549,552 A | 10/1985 | Groch et al. |
| 4,596,255 A | 6/1986 | Snell et al. |
| 4,601,291 A | 7/1986 | Boute et al. |
| 4,680,708 A | 7/1987 | Ambos et al. |
| 4,791,936 A | 12/1988 | Snell et al. |
| 4,800,883 A | 1/1989 | Winstrom |
| 4,802,491 A | 2/1989 | Cohen et al. |
| 4,809,697 A | 3/1989 | Causey, III et al. |
| 4,825,869 A | 5/1989 | Sasmor et al. |
| 4,850,357 A | 7/1989 | Bach, Jr. |
| 4,944,298 A | 7/1990 | Sholder |
| 4,947,857 A | 8/1990 | Albert et al. |
| 4,958,632 A | 9/1990 | Duggan |
| 4,964,410 A | 10/1990 | Leahey et al. |
| 4,974,598 A | 12/1990 | John |
| 4,979,506 A | 12/1990 | Silvian |
| 4,989,610 A | 2/1991 | Patton et al. |

(Continued)

FOREIGN PATENT DOCUMENTS

EP    0491649    6/1992

(Continued)

*Primary Examiner* — Scott Getzow
*Assistant Examiner* — Joseph Dietrich
(74) *Attorney, Agent, or Firm* — Schwegman, Lundberg & Woessner, P.A.

(57) ABSTRACT

Methods, systems, and computer program products differentiate between arrhythmic events having different origins. An implantable medical device detects the arrhythmic events. At least one method involves receiving electrograms representing arrhythmic events and sorting the arrhythmic events into groups based on similarities between the electrograms and/or differences between the electrograms. The method also involves identifying an exemplary arrhythmic event from each group to represent the group from which the exemplary arrhythmic event is identified and distinguishing each exemplary arrhythmic event via an interface display.

20 Claims, 10 Drawing Sheets

U.S. PATENT DOCUMENTS

| | | | |
|---|---|---|---|
| 4,998,531 A | 3/1991 | Bocchi et al. | |
| 5,000,189 A | 3/1991 | Throne et al. | |
| 5,012,814 A | 5/1991 | Mills et al. | |
| 5,027,824 A | 7/1991 | Dougherty et al. | |
| 5,046,504 A | 9/1991 | Albert et al. | |
| 5,047,930 A | 9/1991 | Martens et al. | |
| 5,050,612 A | 9/1991 | Matsumura | |
| 5,052,395 A | 10/1991 | Burton et al. | |
| 5,111,816 A | 5/1992 | Pless et al. | |
| 5,113,869 A | 5/1992 | Nappholz et al. | |
| 5,129,392 A | 7/1992 | Bardy et al. | |
| 5,184,614 A | 2/1993 | Collins et al. | |
| 5,193,550 A | 3/1993 | Duffin | |
| 5,209,228 A | 5/1993 | Cano et al. | |
| 5,213,098 A | 5/1993 | Bennett et al. | |
| 5,215,083 A | 6/1993 | Drane et al. | |
| 5,217,021 A | 6/1993 | Steinhaus et al. | |
| 5,224,475 A | 7/1993 | Berg et al. | |
| 5,273,049 A | 12/1993 | Steinhaus et al. | |
| 5,279,293 A | 1/1994 | Andersen et al. | |
| 5,292,341 A | 3/1994 | Snell | |
| 5,299,118 A | 3/1994 | Martens et al. | |
| 5,309,919 A | 5/1994 | Snell et al. | |
| 5,311,873 A | 5/1994 | Savard et al. | |
| 5,311,874 A | 5/1994 | Baumann et al. | |
| 5,312,441 A | 5/1994 | Mader et al. | |
| 5,315,512 A | 5/1994 | Roth | |
| 5,341,811 A | 8/1994 | Cano | |
| 5,342,402 A | 8/1994 | Olson et al. | |
| 5,344,430 A | 9/1994 | Berg et al. | |
| 5,357,969 A | 10/1994 | Herleikson | |
| 5,391,188 A | 2/1995 | Nelson et al. | |
| 5,402,794 A | 4/1995 | Wahlstrand et al. | |
| 5,404,877 A | 4/1995 | Nolan et al. | |
| 5,404,880 A | 4/1995 | Throne | |
| 5,411,530 A | 5/1995 | Akhtar | |
| 5,413,594 A | 5/1995 | Williams | |
| 5,417,714 A | 5/1995 | Levine et al. | |
| 5,421,830 A | 6/1995 | Epstein et al. | |
| 5,423,871 A | 6/1995 | Hoegnelid et al. | |
| 5,431,692 A | 7/1995 | Hansen et al. | |
| 5,458,623 A | 10/1995 | Lu et al. | |
| 5,464,433 A | 11/1995 | White et al. | |
| 5,476,485 A | 12/1995 | Weinberg et al. | |
| 5,487,754 A | 1/1996 | Snell et al. | |
| 5,487,755 A | 1/1996 | Snell et al. | |
| 5,496,351 A | 3/1996 | Plicchi et al. | |
| 5,507,786 A | 4/1996 | Morgan et al. | |
| 5,511,553 A | 4/1996 | Segalowitz | |
| 5,513,645 A | 5/1996 | Jacobson et al. | |
| 5,535,753 A | 7/1996 | Petrucelli et al. | |
| 5,549,646 A | 8/1996 | Katz et al. | |
| 5,549,654 A | 8/1996 | Powell | |
| 5,555,888 A | 9/1996 | Brewer et al. | |
| 5,578,063 A | 11/1996 | Bocek et al. | |
| 5,584,298 A | 12/1996 | Kabal | |
| 5,586,556 A | 12/1996 | Spivey et al. | |
| 5,591,214 A | 1/1997 | Lu | |
| 5,603,331 A | 2/1997 | Heemels et al. | |
| 5,607,460 A | 3/1997 | Kroll et al. | |
| 5,609,612 A | 3/1997 | Plicchi et al. | |
| 5,609,615 A | 3/1997 | Sanders et al. | |
| 5,613,495 A | 3/1997 | Mills et al. | |
| 5,620,474 A | 4/1997 | Koppman | |
| 5,626,620 A | 5/1997 | Kieval et al. | |
| 5,626,623 A | 5/1997 | Kieval et al. | |
| 5,628,321 A | 5/1997 | Scheib et al. | |
| 5,628,776 A | 5/1997 | Paul et al. | |
| 5,643,255 A | 7/1997 | Organ | |
| 5,647,369 A | 7/1997 | Petrucelli et al. | |
| 5,653,737 A | 8/1997 | van Lake | |
| 5,674,249 A | 10/1997 | de Coriolis et al. | |
| 5,683,431 A | 11/1997 | Wang | |
| 5,687,737 A | 11/1997 | Branham et al. | |
| 5,693,075 A | 12/1997 | Plicchi et al. | |
| 5,697,959 A | 12/1997 | Poore | |
| 5,709,712 A | 1/1998 | Paul et al. | |
| 5,713,366 A | 2/1998 | Armstrong et al. | |
| 5,716,383 A | 2/1998 | Kieval et al. | |
| 5,716,384 A | 2/1998 | Snell | |
| 5,722,999 A | 3/1998 | Snell | |
| 5,724,985 A | 3/1998 | Snell et al. | |
| 5,732,708 A | 3/1998 | Nau et al. | |
| 5,743,268 A | 4/1998 | Kabal | |
| 5,749,900 A | 5/1998 | Schroeppel et al. | |
| 5,749,906 A | 5/1998 | Kieval et al. | |
| 5,749,907 A | 5/1998 | Mann | |
| 5,755,742 A | 5/1998 | Schuelke et al. | |
| 5,759,196 A | 6/1998 | Hess et al. | |
| 5,759,199 A | 6/1998 | Snell et al. | |
| 5,772,604 A | 6/1998 | Langberg et al. | |
| 5,782,890 A | 7/1998 | Wahlstrand et al. | |
| 5,788,640 A | 8/1998 | Peters | |
| 5,788,717 A * | 8/1998 | Mann et al. | 607/14 |
| 5,792,203 A | 8/1998 | Schroeppel | |
| 5,792,204 A | 8/1998 | Snell | |
| 5,792,207 A | 8/1998 | Dietrich | |
| 5,814,083 A | 9/1998 | Hess et al. | |
| 5,814,088 A | 9/1998 | Paul et al. | |
| 5,817,137 A | 10/1998 | Kaemmerer | |
| 5,833,623 A | 11/1998 | Mann et al. | |
| 5,876,353 A | 3/1999 | Riff | |
| 5,891,043 A | 4/1999 | Ericksen et al. | |
| 5,891,178 A | 4/1999 | Mann et al. | |
| 5,891,179 A | 4/1999 | Er et al. | |
| 5,897,577 A | 4/1999 | Cinbis et al. | |
| 5,924,989 A | 7/1999 | Polz | |
| 5,925,067 A | 7/1999 | Lu | |
| 5,951,484 A | 9/1999 | Hoium et al. | |
| 5,954,664 A | 9/1999 | Seegobin | |
| 5,957,861 A | 9/1999 | Combs et al. | |
| 5,961,467 A | 10/1999 | Shimazu et al. | |
| 5,974,341 A | 10/1999 | Er et al. | |
| 5,978,707 A | 11/1999 | Krig et al. | |
| 6,004,276 A | 12/1999 | Wright et al. | |
| 6,007,493 A | 12/1999 | Ericksen et al. | |
| 6,016,442 A | 1/2000 | Hsu et al. | |
| 6,016,446 A | 1/2000 | Belalcazar | |
| 6,016,447 A | 1/2000 | Juran et al. | |
| 6,016,448 A | 1/2000 | Busacker et al. | |
| 6,017,307 A | 1/2000 | Raines | |
| 6,035,233 A | 3/2000 | Schroeppel et al. | |
| 6,067,471 A | 5/2000 | Warren | |
| 6,076,015 A | 6/2000 | Hartley et al. | |
| 6,091,990 A * | 7/2000 | Hsu et al. | 607/5 |
| 6,095,984 A | 8/2000 | Amano et al. | |
| 6,101,415 A | 8/2000 | Er et al. | |
| 6,108,577 A | 8/2000 | Benser | |
| 6,112,117 A | 8/2000 | KenKnight et al. | |
| 6,179,865 B1 | 1/2001 | Hsu et al. | |
| 6,223,078 B1 | 4/2001 | Marcovecchio | |
| 6,243,606 B1 | 6/2001 | Mann et al. | |
| 6,253,102 B1 | 6/2001 | Hsu et al. | |
| 6,263,244 B1 | 7/2001 | Mann et al. | |
| 6,266,554 B1 * | 7/2001 | Hsu et al. | 600/515 |
| 6,275,732 B1 | 8/2001 | Hsu et al. | |
| 6,289,244 B1 | 9/2001 | Conley et al. | |
| 6,289,248 B1 | 9/2001 | Conley et al. | |
| 6,301,503 B1 | 10/2001 | Hsu et al. | |
| 6,308,095 B1 | 10/2001 | Hsu et al. | |
| 6,311,089 B1 | 10/2001 | Mann et al. | |
| 6,312,378 B1 | 11/2001 | Bardy | |
| 6,312,388 B1 | 11/2001 | Marcovecchio et al. | |
| 6,415,175 B1 | 7/2002 | Conley et al. | |
| 6,418,340 B1 | 7/2002 | Conley et al. | |
| 6,449,503 B1 | 9/2002 | Hsu | |
| 6,449,504 B1 | 9/2002 | Conley et al. | |
| 6,456,871 B1 | 9/2002 | Hsu et al. | |
| 6,459,929 B1 | 10/2002 | Hopper et al. | |
| 6,459,934 B1 | 10/2002 | Kadhiresan | |
| 6,477,404 B1 | 11/2002 | Yonce et al. | |
| 6,493,579 B1 | 12/2002 | Gilkerson et al. | |
| 6,522,925 B1 | 2/2003 | Gilkerson et al. | |
| 6,526,313 B2 | 2/2003 | Sweeney et al. | |
| 6,535,763 B1 | 3/2003 | Hiebert et al. | |
| 6,665,558 B2 | 12/2003 | Kalgren et al. | |
| 6,718,198 B2 | 4/2004 | Conley et al. | |

| | | |
|---|---|---|
| 6,721,594 B2 | 4/2004 | Conley et al. |
| 6,748,269 B2 | 6/2004 | Thompson et al. |
| 6,843,801 B2 | 1/2005 | Conley et al. |
| 7,031,764 B2 | 4/2006 | Schwartz et al. |
| 7,203,535 B1 | 4/2007 | Hsu et al. |
| 7,212,849 B2 | 5/2007 | Zhang et al. |
| 7,418,295 B2 | 8/2008 | Conley et al. |
| 7,430,446 B2 | 9/2008 | Li |
| 2002/0077859 A1 | 6/2002 | Stahmann et al. |
| 2002/0151809 A1 | 10/2002 | Conley et al. |
| 2003/0114891 A1 | 6/2003 | Hiebert et al. |
| 2004/0082976 A1 | 4/2004 | Kalgren et al. |
| 2005/0107840 A1 | 5/2005 | Conley et al. |
| 2005/0256544 A1 | 11/2005 | Thompson |
| 2006/0281998 A1 | 12/2006 | Li |
| 2007/0149890 A1 | 6/2007 | Li et al. |
| 2009/0036942 A1 | 2/2009 | Conley et al. |

FOREIGN PATENT DOCUMENTS

| | | |
|---|---|---|
| EP | 0558353 | 9/1993 |
| EP | 0565084 | 10/1993 |
| EP | 0711531 | 5/1996 |
| EP | 0850661 | 7/1998 |
| WO | WO-99/27992 | 6/1999 |

* cited by examiner

COMPARED
ELECTROGRAM

GROUP 1

GROUP 2

GROUP N

DIFFERENTIATING ARRHYTHMIC EVENTS HAVING DIFFERENT ORIGINS

TECHNICAL FIELD

The present invention relates generally to medical devices and systems and appliances for interfacing with medical devices. More particularly, the present invention is directed to classifying and highlighting arrhythmic events detected by a implantable medical device.

BACKGROUND

Pulse generators, such as pacemakers and implantable cardiac defibrillators, record numerous electrograms associated with arrhythmic events or episodes. More than one type of arrhythmia may fall within a single detection zone for a patient. Thus, a clinician needs to inspect the recorded electrograms to assess a cause of each arrhythmia. Further, the same arrhythmia may occur many times in the same patient, leading to the presentation of many occurrences of the same condition for a clinician to review.

Some patient management systems include entire collections of episodes recorded for patients since device implant. This data is made available for user assessment via user interfaces. Reviewing hundreds of recorded episodes to assess patient trends can be tedious and time consuming for clinicians. Other factors, such as assessing recorded heart rates, values of detection-related variables, and the quantity and types of therapies delivered can also contribute to user data overload.

Some conventional programmer applications reduce the number of displayed arrhythmic events by filtering based on initial detection zone or by range of dates. However, this approach does not distinguish between different arrhythmias in the same zone or the same type of arrhythmia detected in different zones.

Accordingly there is an unaddressed need in the industry to address the aforementioned and other deficiencies and inadequacies.

SUMMARY

This Summary is provided to introduce a selection of concepts in simplified form that are further described below in the Detailed Description. This Summary is not intended to identify key features or essential features of the claimed subject matter, nor is the Summary intended for use as an aid in determining the scope of the claimed subject matter.

In accordance with the present invention, the above and other problems are solved by embodiments of the present invention. Embodiments of the present invention are directed to methods, systems, and computer program products for differentiating arrhythmic events having different origins. Embodiments of the present invention utilize electrograms recorded by an implantable medical device to identify groups of episodes or arrhythmic events similar in origin. Electrogram signal waveforms are compared between episodes to detect waveforms that are similar. One arrhythmic event from each group of similar events is identified for highlighting or display. This data display technique can speed clinician review of recorded episodes by focusing attention on classes of arrhythmia that a patient has experienced and that the implantable medical device has detected.

One embodiment of the present invention is a method for differentiating between arrhythmic events having different origins. An implantable medical device detects the arrhythmic events. The method involves receiving electrograms representing arrhythmic events and sorting the arrhythmic events into groups based on similarities between the electrograms and/or differences between the electrograms. The method also involves identifying an exemplary arrhythmic event from each group to represent the group from which the exemplary arrhythmic event is identified and distinguishing each exemplary arrhythmic event via an interface display.

Another embodiment of the present invention is a computer program product comprising a computer-readable medium having control logic stored therein for causing a computing apparatus to differentiate between arrhythmic events detected in a patient. The control logic includes computer-readable program code for causing the computing apparatus to receive electrograms representing arrhythmic events and sort the arrhythmic events into groups based on similarities between the electrograms and/or differences between the electrograms. The control logic also includes computer-readable program code for causing the computing apparatus to identify an exemplary arrhythmic event from each group to represent the group from which the exemplary arrhythmic event is identified and distinguish each exemplary arrhythmic event via an interface display.

Still another embodiment of the present invention is a computer-implemented system for differentiating between arrhythmic events having different origins. The system includes an external programmer operative to receive electrograms representing arrhythmic events detected by an implantable medical device, sort the arrhythmic events into groups based on similarities between the electrograms, and identify an exemplary arrhythmic event from each group to represent the group. The external programmer is also operative to highlight or display each exemplary arrhythmic event via an interface display.

Aspects of the invention may be implemented as a computer process, a computing system, or as an article of manufacture such as a computer program product or computer-readable medium. The computer program product may be a computer storage media readable by a computer system and encoding a computer program of instructions for executing a computer process. The computer program product may also be a propagated signal on a carrier readable by a computing system and encoding a computer program of instructions for executing a computer process.

Other apparatuses, computer program products, methods, features, systems, and advantages of the present invention will be or become apparent to one with skill in the art upon examination of the following drawings and detailed description. It is intended that all such additional apparatuses, methods, systems, features, and advantages be included within this description, be within the scope of the present invention, and be protected by the accompanying claims.

DETAILED DESCRIPTION

As described briefly above, embodiments of the present invention provide methods, computer program products, and systems for differentiating arrhythmic events having different origins. Intracardiac electrograms recorded for arrhythmic episodes by an implantable medical device, such as a pulse generator, are used to identify groups of episodes similar in origin. In the following detailed description, references are made to accompanying drawings that form a part hereof, and in which are shown by way of illustration specific embodiments or examples. These embodiments may be combined, other embodiments may be utilized, and structural changes may be made without departing from the spirit and scope of the present invention. The following detailed description is, therefore, not to be taken in a limiting sense, and the scope of the present invention is defined by the appended claims and their equivalents.

Figure 1:
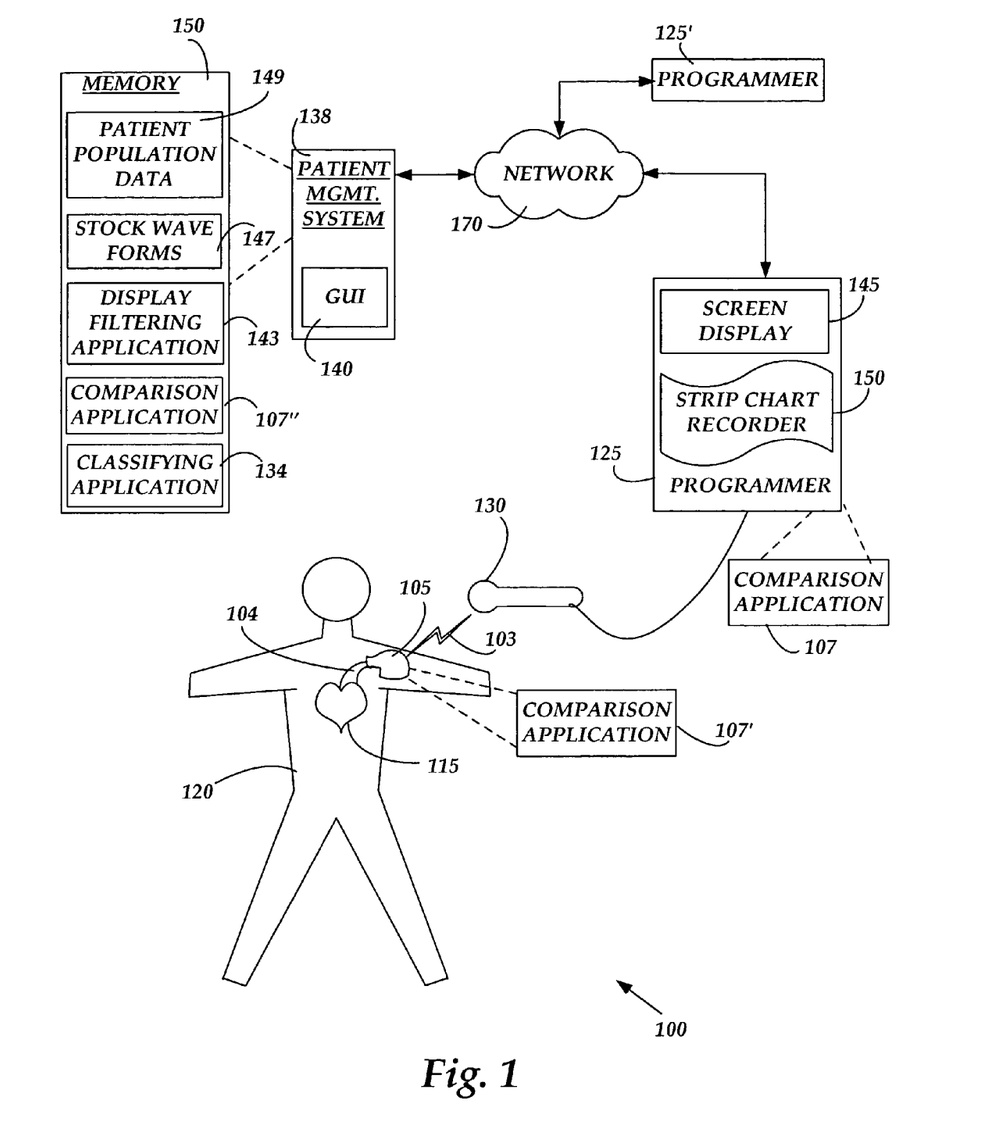
FIG. 1 is a schematic drawing illustrating components of an illustrative embodiment of the present invention and an operating environment in which the embodiment may be utilized.
Figure 2:
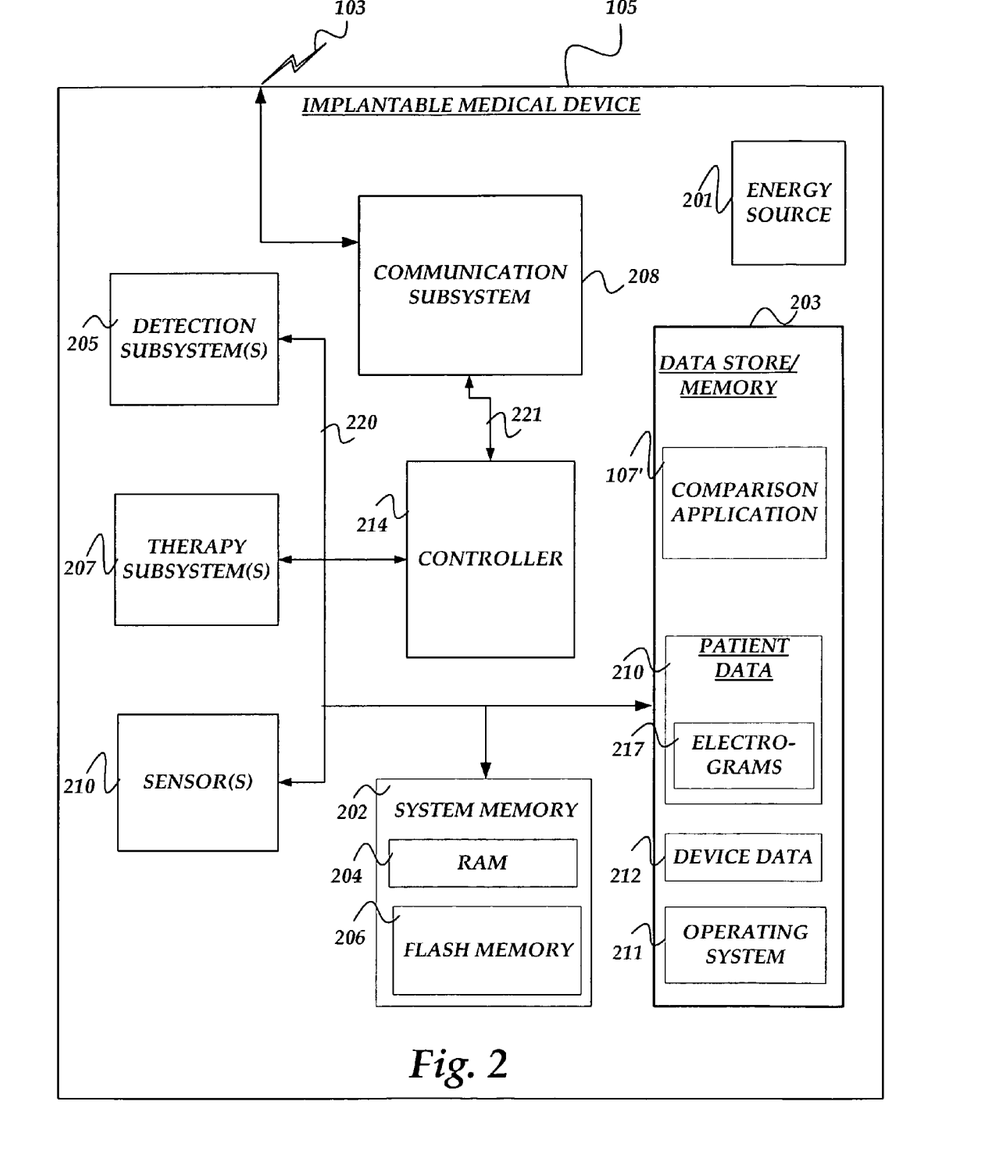
FIG. 2 illustrates computing system architecture for an implantable medical device utilized in an illustrative embodiment of the present invention.
Figure 3:
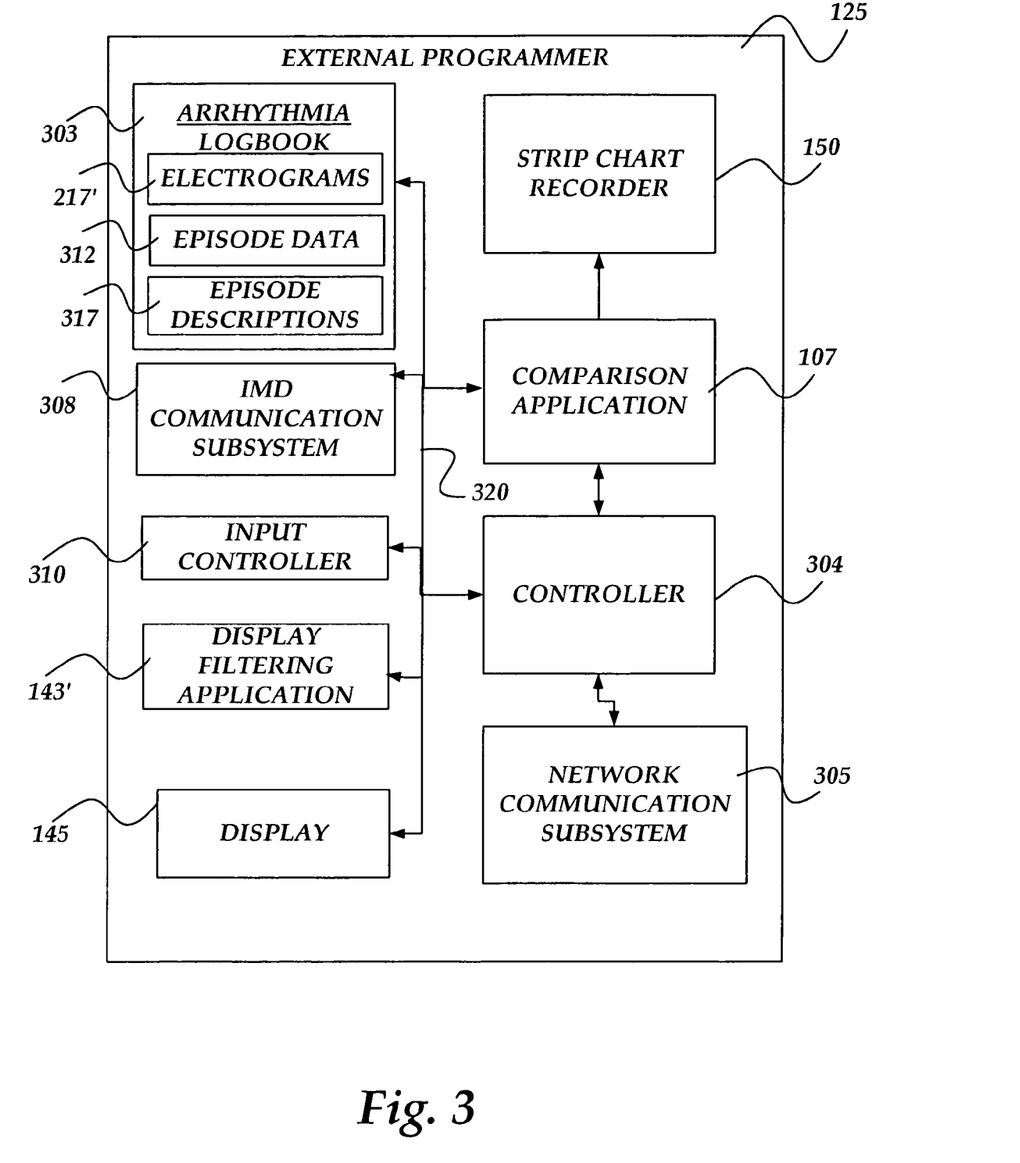
FIG. 3 illustrates computing system architecture for an external programmer utilized in an illustrative embodiment of the present invention.

Referring now to the drawings, in which like numerals represent like elements through the several figures, aspects of the present invention and the exemplary operating environment will be described. FIGS. 1-3 and the following discussion are intended to provide a brief, general description of a suitable computing environment in which the embodiments of the invention may be implemented. While the invention will be described in the general context of program modules that execute to differentiate arrhythmic events having different origins, those skilled in the art will recognize that the invention may also be implemented in combination with other program modules.

Generally, program modules include routines, programs, components, data structures, and other types of structures that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules may be located in both local and remote memory storage devices.

The present embodiments of the invention will be described in applications involving implantable medical devices including, but not limited to, implantable cardiac rhythm management systems such as pacemakers, defibrillators, and biventricular or other multi-site coordination devices. However it is understood that the present methods, systems, and computer program products may be employed in un-implanted devices, including, but not limited to, external pacemakers, cardioverter/defibrillators, pacer/defibrillators, biventricular or other multi-site coordination devices, monitors, programmers, and recorders.

Referring now to FIG. 1, a networked and/or wireless operating environment 100 utilized in embodiments of the present invention that differentiate arrhythmic events having different origins will be described. As shown in FIG. 1, the operating environment includes the medical device (IMD) 105, such as an implantable pulse generator. The IMD) 105 is implanted in a patient 120 and coupled to the heart 115 of the patient 120 by one or more leads 104. The IMD 105 may include a comparison application (CA) 107' for differentiating arrhythmic events by sorting electrograms based on similarity and/or differences between them. Additional details regarding the architecture of the implantable medical device 105 will be described below with respect to FIG. 2.

The operating environment 100 also includes portable computing devices or systems, such as one or more external programmers 125. The external programmer 125 includes a screen display 145 and a strip chart recorder 150. The external programmer also includes a CA 107 for differentiating arrhythmic events by sorting electrograms based on similarity and/or differences between them. Each portable device may serve as a patient, clinician, or physician terminal and are adapted to be communicatively coupled to the medical device 105. Each portable device radiates a wireless signal and may receive wireless signals 103 from the implantable medical device 105. Any wireless protocol, such as microwave, cellular telephony, 802.11, may be used to transmit electrograms from the IMD 105 to a portable device. Each portable device may also transmit data to a server computer, such as a patient management system (PMS) 138 via the network 170. Additional details regarding the external programmer 125 will be described below with respect to FIG. 3.

The PMS 138 may store an entire collection of arrhythmic episodes recorded for one or more patients since each medical device was implanted. The PMS 138 includes a classifying application 134 for determining a rhythm type of each group of electrograms based on patient population data 149 and comparison with stock electrogram waveforms 147 stored on a memory 150. The PMS 138 may also include a CA 107" for differentiating arrhythmic events by sorting electrograms based on similarity and/or differences between them. A display filtering application 143 is also included to distinguish representative or exemplary arrhythmic events via a GUI 140. This technique can be used to reduce user data overload in the GUI 140. Additional details regarding sorting and displaying arrhythmic events will be described below with respect to FIGS. 4-9.

FIG. 2 shows a block diagram illustrating computing system architecture for the IMD 102 utilized in an embodiment of the present invention. The IMD 102 includes a communications subsystem 208, for example a telemetry module, a controller 114, an energy source 201, a system memory 202, and a system bus 220 that couples the system memory 202 to the controller 214. The system memory 202 includes flash memory 206 and random access memory (RAM) 204. The IMD 105 also includes a detection subsystem 205 operable to detect arrhythmias among other features, a therapy subsystem 207, and sensor(s) 210. The IMD 105 further includes a data store/memory (DSM) 203 for storing an operating system 211, the CA 107', patient data 210, and device data 212. The patient data 210 may include all patient diagnostic information. The device data 212 may include device information as well as information from other medical devices in communication with the implantable pulse generator, such as another implantable sensor. It should also be appreciated that the operating system 211 may be a proprietary kernel/executive or a traditional operating system such as WINDOWS from Microsoft Corporation.

The CA 107' in cooperation with the controller 214 is operative to differentiate arrhythmic events by sorting electrograms based on similarity and/or differences between them. The CA 107' may also be stored in the flash memory 206 or RAM 204. The DSM 203 is connected to the controller 214 through a mass storage controller (not shown) connected to the system bus 220. The DSM 203 and its associated computer-readable media, provide non-volatile storage for the IMD 102. Although the description of computer-readable media contained herein refers to a data storage device, such as a hard disk or CD-ROM drive, it should be appreciated by those skilled in the art that computer-readable media can be any available media that can be accessed by the controller 214.

The communications subsystem 208 receives signals from and sends signals to the controller 214 through the signal bus 220. The communications subsystem 208 may or may not use circuitry such as that known in the art for implantable device communications. The IMD 105 radiates signals 103 that also have encoded information, such as electrogram waveforms being communicated from the IMD 105 to a portable device or over the network 170 to the PMS 138. The intracardia electrograms 217 recorded foe each arrhythmic episode by the IMD 105 are used to identify groups of episodes similar in origin. Additional details regarding the comparing and sorting electrograms will be described below with respect to FIG. 4.

Figure 7:
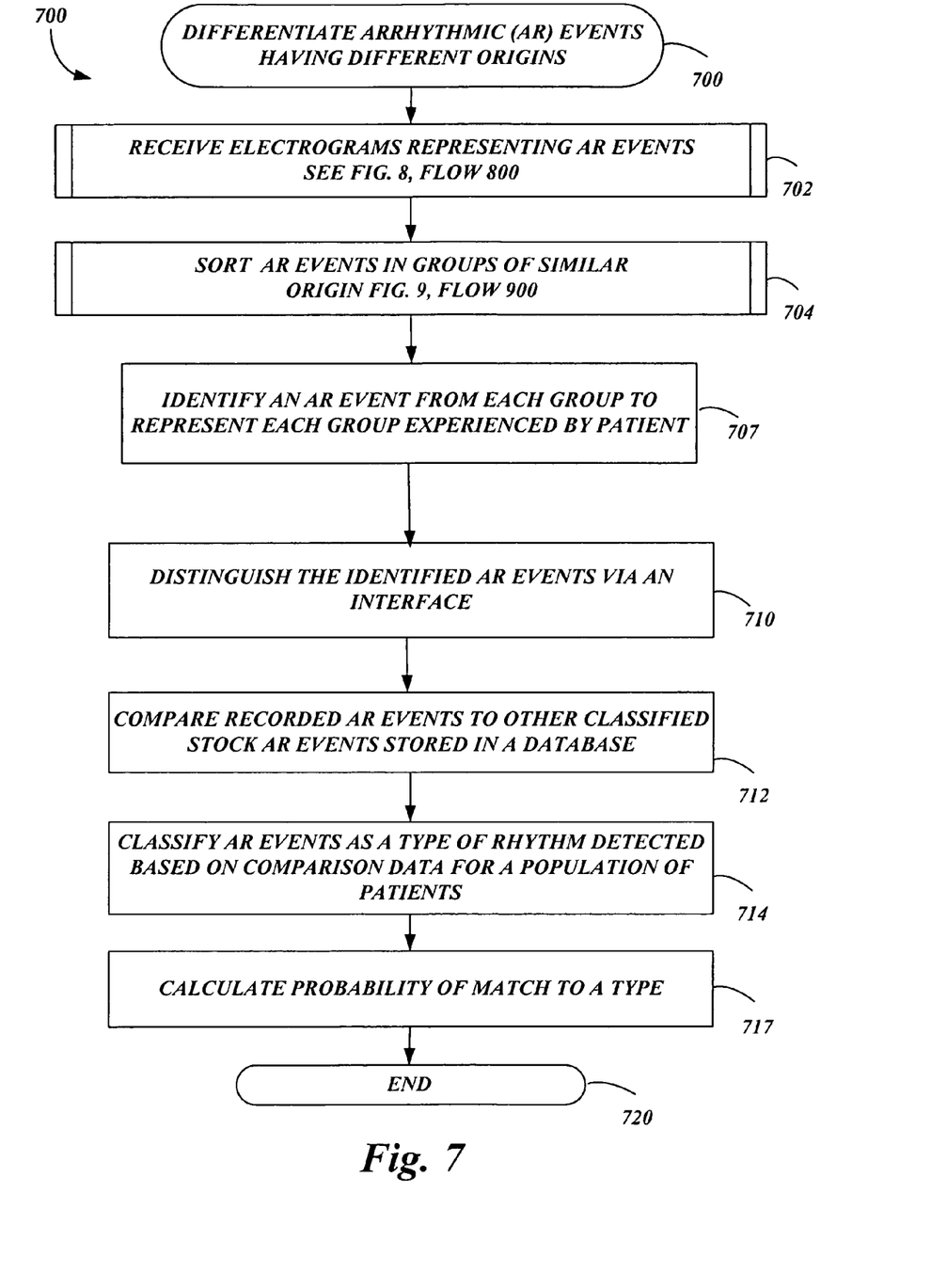
FIG. 7 illustrates an operational flow performed in differentiating arrhythmic events having different origins according to an illustrative embodiment of the present invention.

The controller 214 may employ various operations, discussed in more detail below with reference to FIGS. 7-9 to provide and utilize the signals propagated between the controller 214 and the communications subsystem 208. The controller 214 may store data to and access data from DSM 203, such as electronic memory or magnetic storage. Data may be collected via the detection subsystem 205, the therapy subsystem 207, and one or more sensors 210 which monitor the patient and the device and facilitate calculations and graphs illustrating the status of the patient and the device. Data is transferred to and received from the DSM 103 through the system bus 220. The controller 214 may be a general-purpose computer controller or processor typically used for an IMD. Furthermore, the controller 214 may be firmware, hard-wired logic, analog circuitry, other special purpose circuitry, or any combination thereof.

According to various embodiments of the invention, the IMD 105 operates in a networked and/or wireless environment, as shown in FIG. 1, using a wireless signal 103 to make logical connections with portable devices and remote computers through the network 170, such as the Internet, an Intranet, or a local area network (LAN). The IMD 105 may connect to the network 170 via the communications subsystem 208 connected to the signal bus 221. It should be appreciated that the communications subsystem 208 may also be utilized to connect to other types of networks and remote computer systems. The communications subsystem 208 may also serve as the interface for receiving and responding to information requests over the network 170.

A computing device, such as the IMD 105, typically includes at least some form of computer-readable media. By way of example, and not limitation, computer-readable media might comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the controller 214.

Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Referring now to FIG. 3, computing system architecture for the external programmer 125 utilized in an illustrative embodiment of the present invention will be described. The radiated signal 103 propagated from the IMD 105 is received by the programmer 125 and is converted to an electrical signal that is transferred to the IMD communications subsystem 308. The IMD communications subsystem 308 may then employ an analog-to-digital conversion to convert the received signal 103 to a data signal that is then passed to the controller 304.

Alternatively, or in addition to feeding received signals to the controller 304, the IMD communications subsystem 308 may feed signals directly to the display device 145 or the strip chart recorder 150 for real-time display of the information encoded on the signal 103 such as electrograms. The controller 304 may also transfer a display signal to the display device 145 through the system bus 320. The display signal may include an information signal produced by the IMD communications subsystem 308. The input controller 310 may also be included with the programmer 125 for receiving and processing input from a number of input devices, including a keyboard, audio and/or voice input, a stylus and/or mouse (not shown).

In addition to feeding received signals to the controller 304, the IMD communications subsystem 308 may feed signals directly to an arrhythmia logbook 303 for storage of multiple episode data. The arrhythmia logbook 303 includes electrograms 217' and episode data 312 such as heart rate, values of detection-related state variables, quantities and types of therapies delivered, and event intervals. The arrhythmia logbook 303 also includes arrhythmia electrogram or episode descriptions 317. Information in the arrhythmia logbook 303 is used by the CA 107 to differentiate between arrhythmic events having different origins. The CA 107 compares electrograms and groups them based on similarities and/or differences between them.

Each electrogram may include one or more signals captured just before detection of the arrhythmia, signals at the point which the IMD 105 detected the arrhythmia, and/or signals just prior to delivery of the first therapy since arrhythmia detection. The CA 107 compares electrogram signals between episodes to detect episodes that are similar in origin. The CA 107 then identifies one episode, an exemplary arrhythmic event, from each group for highlighting or display via the display 145. The display filtering application 143' highlights the identified episodes among other episodes and/or lists descriptive text of each identified episode via the display 145. Additional details regarding comparing and displaying the episodes will be described below with respect to FIGS. 4 and 9.

Figure 4:
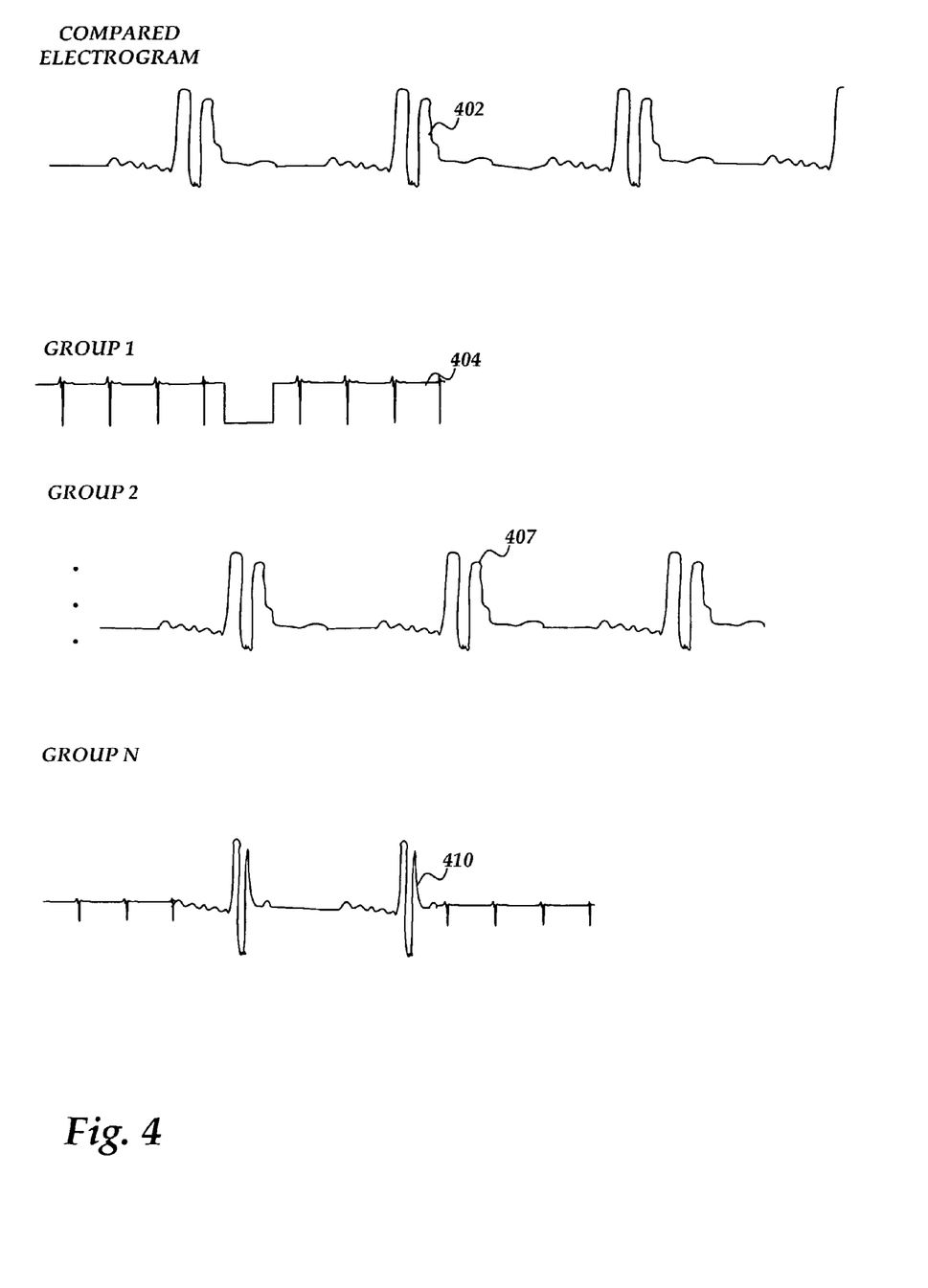
FIG. 4 illustrates an electrogram waveform comparison sorting arrhythmic events into groups according to an illustrative embodiment of the present invention.

FIG. 4 illustrates an electrogram waveform comparison that sorts arrhythmic events into groups according to an illustrative embodiment of the present invention. The CA 107 compares electrograms with other electrograms detected by the IMD 105. For example, an electrogram 402 representing an arrhythmic event is compared with exemplary electrograms 404 representing GROUP 1, 407 representing GROUP 2, and 410 representing GROUP N. As illustrated, the electrogram 402 correlates closely with the electrogram 407. Thus, the CA 107 sorts the electrogram 402 into GROUP 2.

The CA 107 compares electrogram waveforms from different episodes using techniques such as temporal cross-correlation, comparing transforms of signals (e.g. Discrete Fourier Transforms, wavelet transforms, and others), mean squared error comparisons of signals after temporal alignment, and user specified criteria. The CA 107 may also enhance the comparison of waveforms by also comparing recorded heart rates, the values of detection-related state variables computed by the IMD 105, and/or quantities and types of therapies delivered.

The CA 107 also identifies one arrhythmic event from each group for highlighting or display. Each episode identified as an exemplary or representative episode can be highlighted in a list of episodes, or the list could be shortened to only the identified episodes. Additional details regarding highlighting and/or displaying arrhythmic events are described below with respect to FIGS. 5-6.

Figure 5:
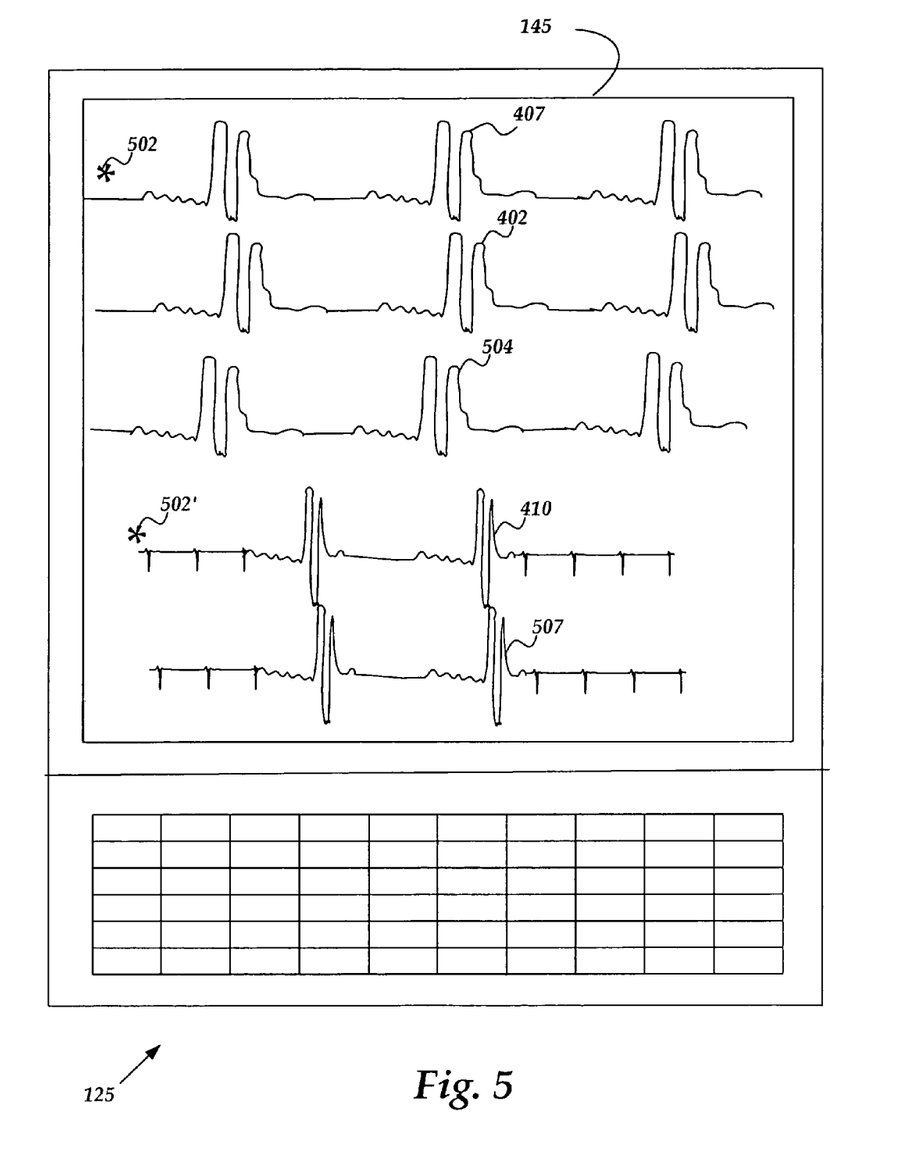
FIG. 5 illustrates a user interface display distinguishing exemplary arrhythmic events according to an illustrative embodiment of the present invention.

FIG. 5 illustrates the user interface display 145 distinguishing exemplary arrhythmic events according to an illustrative embodiment of the present invention. The display filtering application (DFA) 143' displays a number of electrograms via the programmer 125 display 145. The display filtering application 143' renders an asterisk "*" 502 next to the electrograms the CA 107 selects for highlighting as exemplary electrograms for groups. Thus, the DFA 143' renders electrograms 407 and 410 as an exemplary electrograms. In contrast, electrograms 402, 504, and 507 are rendered without highlighting. In the alternative, the DFA 143' may highlight the selected electrograms with color shading.

Figure 6A:
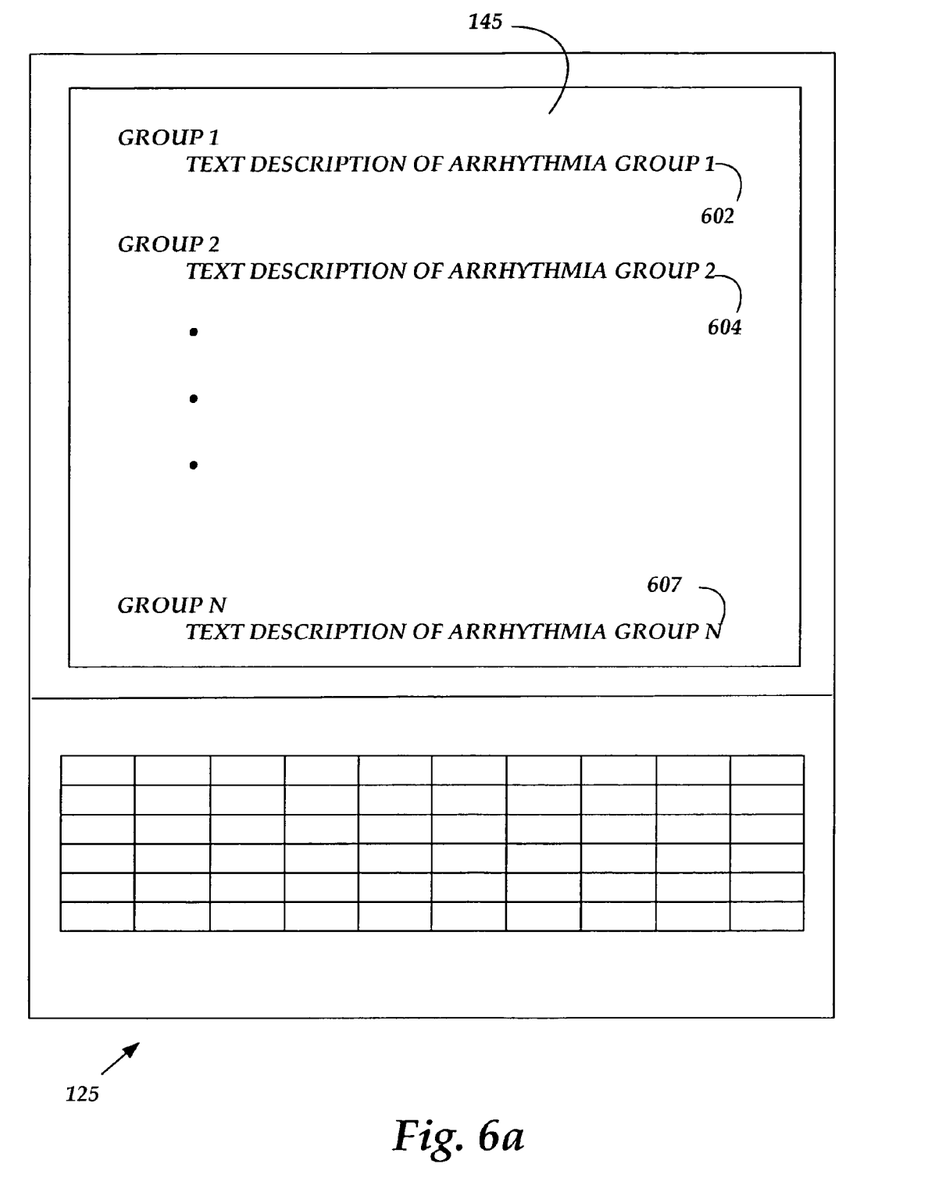
FIGS. 6a-6b illustrate user interface displays distinguishing exemplary arrhythmic events according to other illustrative embodiments of the present invention.

Similarly, FIG. 6a illustrates the user interface display 145 distinguishing exemplary arrhythmic events according to another illustrative embodiment of the present invention. The DFA 143' renders descriptive text 602, 604, and 607 for each group of arrhythmia detected by the IMD 105 for a given patient. The programmer 125 includes the arrhythmia logbook 303. The arrhythmia logbook 303 includes the episode descriptions 317 which are essentially text lists with a high-level description of each episode. The DFA 143' uses these high-level descriptions to differentiate arrhythmic events having different origins via the display 145. It should be appreciated that upon selection of the descriptive text for any group, the display 145 renders the descriptive text for all detected arrhythmias in the selected group.

Figure 6B:
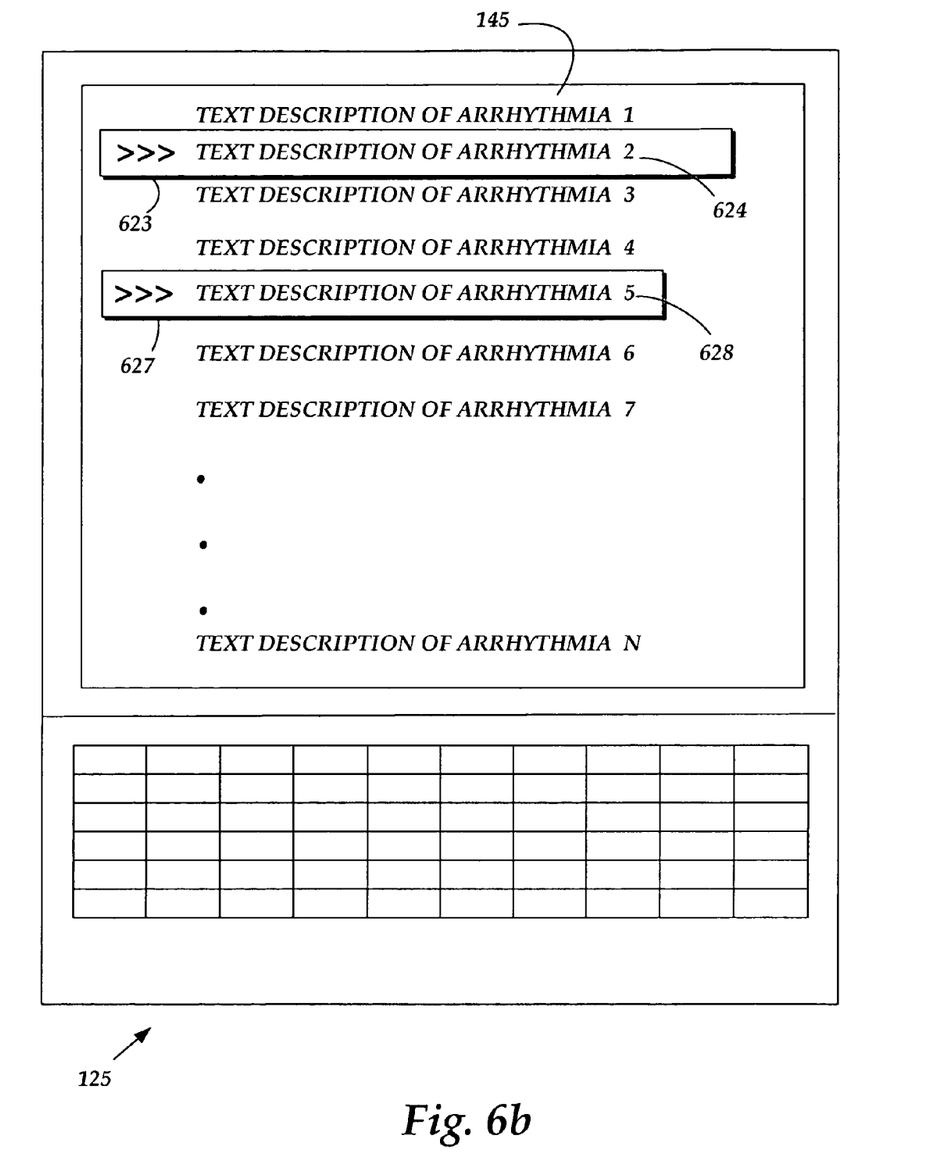

Still further, FIG. 6b illustrates the user interface display 145 distinguishing exemplary arrhythmic events according to still another illustrative embodiment of the present invention. The DFA 143' renders descriptive text for each of a plurality of arrhythmia 1-N detected by the IMD 105 for a given patient. The DFA 143' differentiates arrhythmic events of different origins by highlighting exemplary descriptive text with highlight bars 623 and 627 via the display 145. Thus, a text description of arrhythmia 624 and a text description of arrhythmia 628 can represent all arrhythmia of different origins detected by the IMD 105 for a given patient.

Turning now to FIGS. 1, 2, 3 and 7, an operational flow 700 performed in differentiating arrhythmic events having different origins according to an illustrative embodiment of the present invention will be described. The logical operations of the various embodiments of the present invention are implemented (1) as a sequence of computer implemented acts or program modules running on a computing system and/or (2) as interconnected machine logic circuits or circuit modules within the computing system. The implementation is a matter of choice dependent on the performance requirements of the computing system or apparatus implementing the invention. Accordingly, the logical operations making up the embodiments of the present invention described herein are referred to variously as operations, structural devices, acts or modules. It will be recognized by one skilled in the art that these operations, structural devices, acts and modules may be implemented in software, in firmware, in special purpose digital logic, and any combination thereof without deviating from the spirit and scope of the present invention as recited within the claims attached hereto.

The operational flow 700 begins at operation 702 where the external programmer 125, or the IMD 105, receives electrograms representing arrhythmic events detected by the IMD 105. Additional details regarding receiving electrograms will be described below with respect to FIG. 8, flow 800. Next at operation 704, the CA 107 sorts arrhythmic events in groups based on similarities and/or differences between the electrograms. Additional details regarding sorting arrhythmic events will be described below with respect to FIG. 9, flow 900.

Next at operation 707, the CA 107 identifies an exemplary arrhythmic event from each group to represent each of different origin experienced by a patient. Next the DFA 143' distinguishes the identified arrhythmic events via the display 145 by highlighting or only displaying the exemplary arrhythmic events as electrograms and/or descriptive text. The operational flow 700 then continues to operation 712.

At operation 712, the classifying application 134 compares recorded arrhythmic event electrograms to other classified stock waveforms 147 collected based on patient population data 149. Then at operation 714, the classifying application 134, classifies arrhythmic events as a type of rhythm based on the comparison with the stock waveforms 147. For instance, the classifying application may classify an arrhythmic event electrogram as monomorphic ventricular tachycardia, polymorphic ventricular tachycardia, or supraventriclar tachycardia. The classifying application may also classify an arrhythmic event electrogram as a junctional rhythm, flutter, fibrillation, or standstill. Next, at operation 714 the classifying application 134 calculates a probability that certain electrograms match a particular stock waveform type. The operational flow then terminates at end operation 720.

Figure 8:
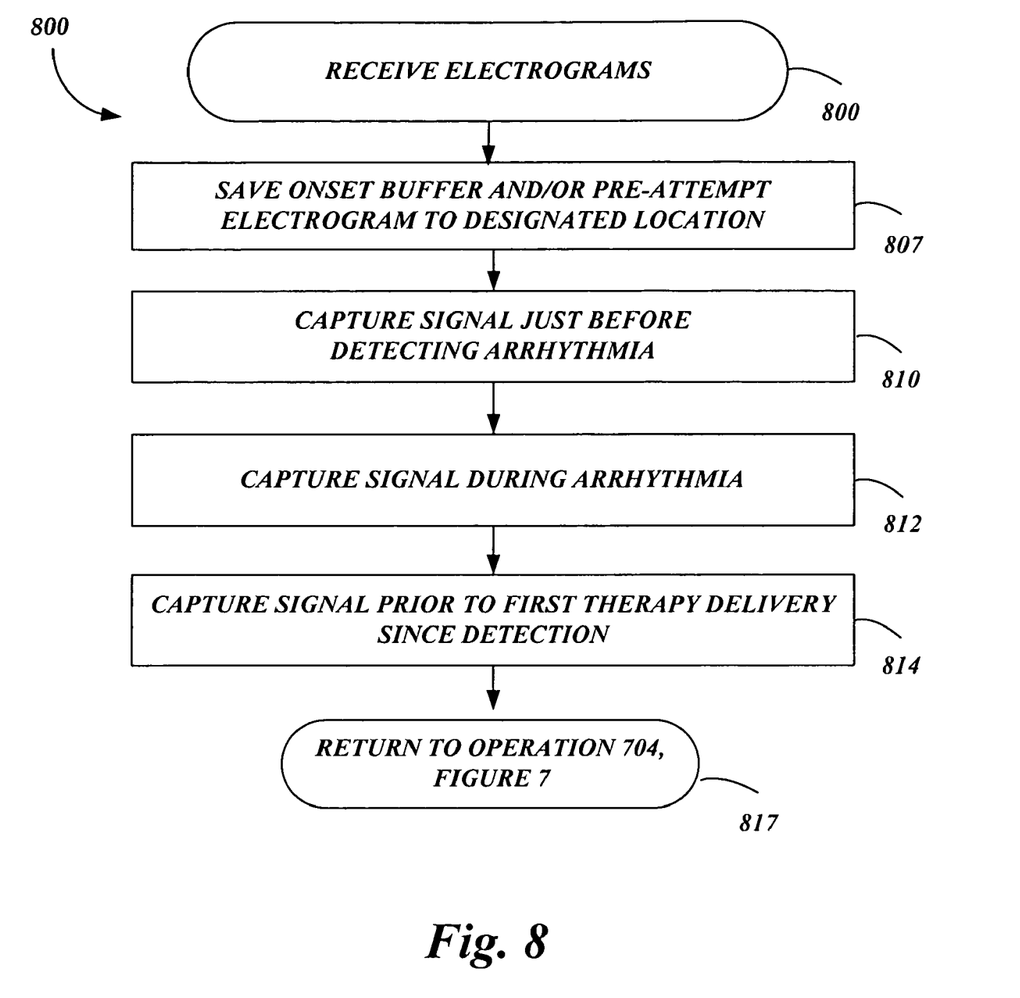
FIG. 8 illustrates an operational flow performed in receiving electrograms representing arrhythmic events according to an illustrative embodiment of the present invention.

FIG. 8 illustrates an operational flow 800 performed in receiving electrograms representing arrhythmic events according to an illustrative embodiment of the present invention. The operational flow 800 begins at operation 807 where the IMD 105 saves an onset buffer and/or a pre-attempt electrogram to a designated location, for example in the IMD 105 memory 203. Upon detecting an episode, the IMD 105 retrieves previously recorded electrogram segments for analysis. The electrograms analyzed for comparison by the CA 107 include an onset buffer and pre-attempt electrograms recorded for an arrhythmic event. In the case of atrial tachycardia response episodes, only the onset buffer is included.

Next at operation 810, the IMD 105 captures a signal just before detecting an arrhythmia. Then at operations 812 and 814, the IMD 105 captures a signal during the arrhythmia and just prior to a first therapy being delivered since detection, respectively. Control then returns to operation 704 of FIG. 7 at return operation 817.

Figure 9:
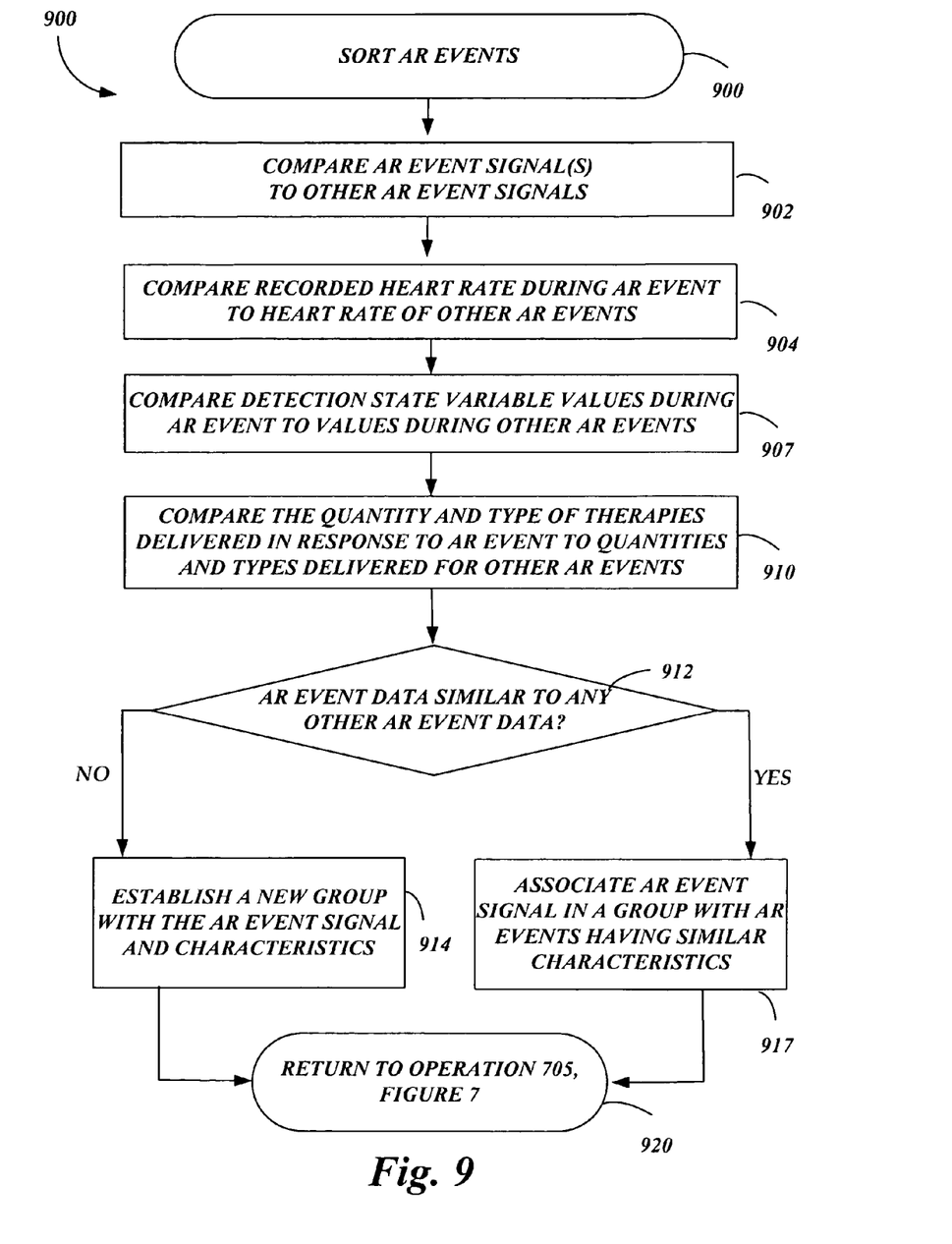
FIG. 9 illustrates an operational flow performed in sorting arrhythmic events into groups based on electrogram comparisons according to an illustrative embodiment of the present invention.

FIG. 9 illustrates an operational flow 900 performed in sorting arrhythmic events into groups based on electrogram comparisons according to an illustrative embodiment of the present invention. The operational flow 900 begins at operation 902 where the CA 107 compares arrhythmic event signals or electrograms to other arrhythmic event signals recorded by the IMD 105.

Next, at operation 904, to enhance the waveform comparison with other comparison data, the CA 107 may compare a heart rate during the episode to heart rate of other episodes. Then at operation 907, the CA 107 compares detection state variable values recorded during an episode to values recorded during other episodes. Examples of state variables that may be included are an atrial rate upon detection of the arrhythmia, a ventricular rate upon detection of the arrhythmia, whether the ventricular rate was higher than the atrial rate upon detection of the arrhythmia, and whether the rate gradually or suddenly increased prior to detection of the arrhythmia. Still further, the CA 107 compares the quantity and/or type of therapies delivered in response to the episode to quantities and types of therapies delivered during other episodes. The operational flow 900 then continues to operation 912.

At operation 912, the CA 107 determines whether the episode is similar to any other episodes or data. When substantial similarities do exist, the operational flow 900 continues from operation 912 to operation 917 where the CA 107 associates the episode in a group with episodes having similar characteristics. Control then returns to operation 705 at return operation 920. In contrast at operation 912 when there are not enough substantial similarities between the compared episode and other episodes, the operational flow 900 continues from operation 912 to operation 914 where the CA 107 establishes a new group with the compared episode and associated data. The operational flow 900 then continues to return operation 920 described above.

Thus, the present invention is presently embodied as methods, systems, computer program products or computer readable mediums encoding computer programs for differentiating arrhythmic events having different origins.

As various changes may be made in the above system elements, software modules and methods without departing from the scope of the invention, it is intended that all matter contained in the above description as shown in the accompanying drawings shall be interpreted as illustrative and not in a limiting sense. Since many embodiments of the invention can be made without departing from the spirit and scope of the invention, the invention resides in the claims hereinafter appended.

I claim:

1. A method for differentiating arrhythmic episodes having different origins, wherein the arrhythmic episodes are detected in a patient by an implantable medical device, the method comprising:
    receiving electrograms that represent the arrhythmic episodes detected by the implantable medical device;
    sorting the arrhythmic episodes into groups based on at least one of similarities between the electrograms or differences between the electrograms;
    identifying an exemplary arrhythmic episode from each group of the groups of the sorted arrhythmic episodes to represent the each group; and
    distinguishing the exemplary arrhythmic episode of the each group by highlighting the exemplary arrhythmic episode among other arrhythmic episodes of the each group via an interface display.

2. The method of claim 1, further comprising:
    comparing each exemplary arrhythmic episode of the identified exemplary arrhythmic episodes to classified stock arrhythmic episodes; and
    classifying the each exemplary arrhythmic episode as a type of rhythm by comparing the each exemplary arrhythmic episode to the classified stock arrhythmic episodes.

3. The method of claim 2, wherein classifying the each exemplary arrhythmic episode includes calculating a probability that the each exemplary arrhythmic episode is of the type of rhythm.

4. The method of claim 3, wherein the type of rhythm comprises one of the following:
    monomorphic tachycardia;
    polymorphic tachycardia;
    supraventricular tachycardia;
    junctional rhythm;
    flutter;
    fibrillation; and
    standstill.

5. The method of claim 3, wherein the type of rhythm comprises a polymorphic rhythm or a monomorphic rhythm.

6. The method of claim 1, wherein receiving the electrograms comprises:
    saving at least one of an onset electrogram or a pre-attempt electrogram to a designated location in response to detecting an arrhythmia; and
    capturing at least one of the following:
        a signal just prior to detecting the arrhythmia;
        a signal during the arrhythmia; and
        a signal just prior to a first therapy delivery since the arrhythmia was detected.

7. The method of claim 1, wherein sorting the arrhythmic episodes into groups comprises:
    comparing a first electrogram representing a first arrhythmic episode of the arrhythmic episodes with electrograms representing other arrhythmic episodes of the arrhythmic episodes;
    determining whether the first electrogram is substantially similar to any of the electrograms representing the other arrhythmic episodes;
    in response to the first electrogram being substantially similar to any of the electrograms representing the other arrhythmic episodes, associating the first electrogram with the any of the electrograms representing the other arrhythmic episodes in a group of electrograms with substantially similar waveforms; and
    in response to the first electrogram not being substantially similar to any of the electrograms representing the other arrhythmic episodes, establishing a new group of arrhythmic episodes detected by the implantable medical device and represented by the first electrogram.

8. The method of claim 7, wherein comparing the first electrogram with the electrograms representing the other arrhythmic episodes utilizes at least one of the following techniques:
    cross correlation of signals;
    signal transform comparison;
    mean squared error comparison of signals; and
    user-specified comparison criteria.

9. The method of claim 7, wherein sorting the arrhythmic episodes further comprises at least one of the following:
 comparing a first heart rate associated with a first arrhythmic episode of the arrhythmic episodes to heart rates associated with other arrhythmic episodes of the arrhythmic episodes represented by electrograms and associating the first arrhythmic episode with a group based on heart rate similarities;
 comparing detection state variable values during the first arrhythmic episode to detection state variable values during the other arrhythmic episodes represented by electrograms and associating the first arrhythmic episode in a group based on similarities between the detection state variable values;
 comparing a quantity of therapies and type of therapy delivered in response to the first arrhythmic episode to quantities of and types of therapies delivered in response to the other arrhythmic episodes represented by electrograms and associating the first arrhythmic episode in a group based on similarities between the quantities and types of therapy delivered.

10. The method of claim 1, wherein identifying the exemplary arrhythmic episode from the each group comprises selecting an exemplary electrogram from the each group.

11. The method of claim 1, wherein identifying the exemplary arrhythmic episode from the each group comprises selecting exemplary descriptive text describing the each group.

12. The method of claim 10, wherein highlighting the exemplary arrhythmic episode comprises:
 highlighting the exemplary electrogram among other electrograms of the each group via the interface display.

13. The method of claim 11, wherein highlighting the exemplary arrhythmic episode comprises:
 highlighting the exemplary descriptive text among other descriptive text of the each group via the interface display.
 displaying only the exemplary descriptive text via the interface display.

14. The method of claim 6, wherein detecting an arrhythmia comprises detecting an atrial tachycardia response (ATR).

15. A computer program product comprising a computer-readable medium having control logic stored therein for causing a computing apparatus to differentiate between arrhythmic episodes detected in a patient, the control logic comprising computer-readable program code for causing the computing apparatus to:
 receive electrograms representing arrhythmic episodes;
 sort the arrhythmic episodes into groups based on similarities between the electrograms;
 identify an exemplary arrhythmic episode from each group of the groups of the sorted arrhythmia episodes to represent the each group; and
 distinguish the identified exemplary arrhythmic episodes by highlighting the identified exemplary arrhythmic episodes among other arrhythmic episodes via an interface display.

16. The computer program product of claim 15, further comprising computer-readable program code for causing the computing apparatus to:
 compare each exemplary arrhythmic episode of the identified exemplary arrhythmic episodes to classified stock arrhythmic episodes; and
 classify the each exemplary arrhythmic episode as a type of rhythm by comparing the each exemplary arrhythmic episode to the classified stock arrhythmic episodes.

17. The computer program product of claim 15, wherein the computer-readable program code for causing the computing apparatus to sort the arrhythmic episodes into groups comprises computer-readable program code for causing the computing apparatus to:
 compare a first electrogram representing a first arrhythmic episode of the arrhythmic episodes with electrograms representing other arrhythmic episodes of the arrhythmic episodes;
 determine whether the first electrogram is substantially similar to any of the electrograms representing the other arrhythmic episodes;
 in response to the first electrogram being substantially similar to any of the electrograms representing the other arrhythmic episodes, associate the first electrogram with the any of the electrograms representing the other arrhythmic episodes in a group of electrograms with substantially similar waveforms; and
 in response to the first electrogram not being substantially similar to any of the electrograms representing the other arrhythmic episodes, establish a new group of arrhythmic episodes represented by the first electrogram.

18. A computer-implemented system for differentiating between arrhythmic episodes having different origins, wherein the arrhythmic episodes are detected in a patient by an implantable medical device, the system comprising:
 an external programmer including an interface display, the external programmer operative to:
  receive electrograms that represent arrhythmic episodes detected by the implantable medical device;
  sort the arrhythmic episodes into groups based on at least one of similarities between the electrograms or differences between the electrograms;
  identify an exemplary arrhythmic episode from each group of the groups of the sorted arrhythmic episodes to represent the each group; and
  distinguish each exemplary arrhythmic episode of the identified exemplary arrhythmic episodes via the interface display by highlighting the each exemplary arrhythmic episode among other arrhythmic episodes.

19. The system of claim 18, further comprising a database, classified stock arrhythmic episodes stored in the database, and a patient management system operative to:
 receive the exemplary arrhythmic episodes representing the groups;
 compare the each exemplary arrhythmic episode to the classified stock arrhythmic episodes stored in the database; and
 classify the each exemplary arrhythmic episode as a type of rhythm by comparing the exemplary arrhythmic episodes to the classified stock arrhythmic episodes.

20. The system of claim 18, wherein the each exemplary arrhythmic episode is represented by one of an exemplary electrogram and exemplary descriptive text, wherein the external programmer operative to distinguish the each exemplary arrhythmic episode via the interface display is operative to one of the following:
 highlight each exemplary electrogram among other electrograms via the interface display; and
 highlight exemplary descriptive text among other descriptive text via the interface display.

* * * * *

UNITED STATES PATENT AND TRADEMARK OFFICE
CERTIFICATE OF CORRECTION

| | | |
|---|---|---|
| PATENT NO. | : 8,046,060 B2 | Page 1 of 1 |
| APPLICATION NO. | : 11/273079 | |
| DATED | : October 25, 2011 | |
| INVENTOR(S) | : Howard D. Simms | |

It is certified that error appears in the above-identified patent and that said Letters Patent is hereby corrected as shown below:

In column 11, lines 29-32, in Claim 12, delete "The method of claim 10, wherein highlighting the exemplary arrhythmic episode comprises:
  highlighting the exemplary electrogram among other electrograms of the each group via the interface display." and
insert -- The method of claim 10, wherein highlighting the exemplary arrhythmic episode comprises highlighting the exemplary electrogram among other electrograms of the each group via the interface display. --, therefor.

In column 11, lines 33-39, in Claim 13, delete "The method of claim 11, wherein highlighting the exemplary arrhythmic episode comprises:
    highlighting the exemplary descriptive text among other descriptive text of the each group via the interface display.
    displaying only the exemplary descriptive text via the interface display." and
insert -- The method of claim 11, wherein highlighting the exemplary arrhythmic episode comprises highlighting the exemplary descriptive text among other descriptive text of the each group via the interface display. --, therefor.

Signed and Sealed this
Seventeenth Day of January, 2012

David J. Kappos
*Director of the United States Patent and Trademark Office*